US007598288B2

(12) United States Patent
Hellberg et al.

(10) Patent No.: US 7,598,288 B2
(45) Date of Patent: Oct. 6, 2009

(54) INHIBITORS OF GLYCOGEN SYNTHASE KINASE-3 (GSK-3) FOR TREATING GLAUCOMA

(75) Inventors: Mark R. Hellberg, Arlington, TX (US); Abbot F. Clark, Arlington, TX (US); Iok-Hou Pang, Grand Prairie, TX (US); Peggy Elizabeth Hellberg, Arlington, TX (US); Loretta Graves McNatt, Hurst, TX (US); Wan-Heng Wang, Grapevine, TX (US)

(73) Assignee: Alcon, Inc., Hunenberg (CH)

( * ) Notice: Subject to any disclaimer, the term of this patent is extended or adjusted under 35 U.S.C. 154(b) by 806 days.

(21) Appl. No.: 10/488,496

(22) PCT Filed: Sep. 23, 2002

(86) PCT No.: PCT/US02/30059

§ 371 (c)(1),
(2), (4) Date: Mar. 2, 2004

(87) PCT Pub. No.: WO03/027275

PCT Pub. Date: Apr. 3, 2003

(65) Prior Publication Data

US 2004/0186159 A1 Sep. 23, 2004

Related U.S. Application Data

(60) Provisional application No. 60/325,390, filed on Sep. 27, 2001.

(51) Int. Cl.
*A61K 31/404* (2006.01)
*A61K 31/4015* (2006.01)
*C12N 9/10* (2006.01)
*C12N 9/12* (2006.01)
*A61K 38/43* (2006.01)
*C12Q 1/48* (2006.01)

(52) U.S. Cl. .................. 514/424; 424/94.5; 435/15; 435/183; 435/194; 514/414

(58) Field of Classification Search ................ 424/94.5; 435/15, 183, 194; 514/414, 424
See application file for complete search history.

(56) References Cited

U.S. PATENT DOCUMENTS

| 5,681,854 | A | 10/1997 | Pang et al. | |
|---|---|---|---|---|
| 5,856,517 | A | 1/1999 | Huryn et al. | |
| 5,891,901 | A | 4/1999 | Dhingra et al. | |
| 6,057,117 | A | 5/2000 | Harrison et al. | |
| 6,255,485 | B1 | 7/2001 | Gray et al. | |
| 6,441,053 | B1 | 8/2002 | Klein et al. | |
| 6,844,335 | B2 * | 1/2005 | Garcia et al. | 514/211.15 |

FOREIGN PATENT DOCUMENTS

| DE | 39 14764 A1 | 11/1990 |
|---|---|---|
| DE | 40 05 969 A1 | 8/1991 |
| DE | 40 05 970 A1 | 8/1991 |
| DE | 42 17 964 A1 | 12/1993 |
| DE | 42 43 321 A1 | 6/1994 |
| EP | 0 328 026 B1 | 2/1989 |
| EP | 0 384 349 B1 | 2/1990 |
| EP | 0 397 060 B1 | 5/1990 |
| EP | 0 470 490 B1 | 7/1991 |
| EP | 0 508 792 A1 | 4/1992 |
| EP | 0 540 956 B1 | 10/1992 |
| WO | WO 93/18765 A1 | 9/1993 |
| WO | WO 93/18766 A1 | 9/1993 |
| WO | WO 95/07910 A1 | 3/1995 |
| WO | WO 96/04906 A1 | 2/1996 |
| WO | WO 98/04551 A1 | 2/1998 |
| WO | WO 98/04552 A1 | 2/1998 |
| WO | WO 98/11102 A1 | 3/1998 |
| WO | WO 98/11103 A1 | 3/1998 |
| WO | WO 99/42100 A1 | 8/1999 |
| WO | WO 99/62503 A2 | 12/1999 |
| WO | WO 99/62503 A3 | 12/1999 |
| WO | WO 00/21927 A2 | 4/2000 |
| WO | WO 00/21927 A3 | 4/2000 |
| WO | WO 00/38675 A1 | 7/2000 |
| WO | WO 01/09106 A1 | 2/2001 |
| WO | WO 01/37819 A2 | 5/2001 |
| WO | WO 01/37819 A3 | 5/2001 |
| WO | WO 01/41768 A3 | 6/2001 |
| WO | WO 01/47533 A2 | 7/2001 |
| WO | WO 01/47533 A3 | 7/2001 |
| WO | WO 01/56567 A1 | 8/2001 |
| WO | WO 01/64949 A2 | 9/2001 |
| WO | WO 01/64949 A3 | 9/2001 |
| WO | WO 01/70727 A1 * | 9/2001 |
| WO | WO 03/027116 A2 | 4/2003 |
| WO | WO 03/027116 A3 | 4/2003 |

OTHER PUBLICATIONS

Hoffman et al. (1999.Pharmacodynamic Aspects of Modes of Drug Administration for Optimization of Drug Therapy. Critical Reviews in Therapeutic Drug Carrier Systems, vol. 16, Issue 6, pp. 1-70.*
Bafico et al., "Interaction of Frizzled Related Protein (FRP) with Wnt Ligands and the Frizzled Receptor Suggests Alternative Mechanisms for FRP Inhibition of Wnt Signaling", J. Biol. Chem., 274(23):16180-16187 (1999).
Berggren, Lennart, "The Intraocular Pressure In Rabbits After Lithium Administration With Comments On Pressure Effects Of Injections Into The Vitreous", Acta Ophthalmologica, 45:229-238 (1967).
Bournat et al., "Wnt-1 Dependent Activation of the Survival Factor NF-•B in PC12 Cells", Journal of Neuroscience Research, 61:21-32 (2000).
Chang et al., "Cloning and characterization of a secreted frizzled-related protein that is expressed by the retinal pigment epithelium", Human Molecular Genetics, 4:575-583 (1999).
Chen et al., "The Mood-Stabilizing Agent Valproate Inhibits the Activity of Glycogen Synthase Kinases-3", Journal of Neurochemistry, 72:1327-1330 (1999).

(Continued)

*Primary Examiner*—Jon P Weber
*Assistant Examiner*—Kailash C Srivastava
(74) *Attorney, Agent, or Firm*—Teresa J. Schultz

(57) ABSTRACT

The use of inhibitors of GSK-3 useful for treating glaucoma is disclosed.

19 Claims, No Drawings

OTHER PUBLICATIONS

Coghlan et al., "Selective small molecule inhibitors of glycogen synthase kinase-3 modulate glycogen metabolism and gene transcription", Chem. & Bio., 7(10):793-803 (2000).

Cross et al., "Selective small-molecule inhibitors of glycogen synthase kinase-3 activity protect primary neurones from death", J. Neurochem., 77:94-102 (2001).

He et al., "Glycogen Synthase Kinase 3• and Extracellular Signal-Regulated Kinase Inactivate Heat Shock Transcription Factor 1 by Facilitating the Disappearance of Transcriptionally Active Granules after Heat Shock", Molecular and Celluar Biology, 18:6624-33 (1998).

Hers et al., "The protein kinase C inhibitors bisindolylmaleimide I (GF 1092303x) and IX (Ro 31-8220) are potent inhibitors of glycogen synthase kinase-3 activity", FEBS Letters, 460:433-436 (1999) listed as Tavaré et al. in appln.

Husain and Abdel-Latif, "Effects of Prostaglandin F2• and Carbachol and MAP Kinases, Cytosolic Phospholipase A2 and Arachidonic Acid Release in Cat Iris Sphincter Smooth Muscle Cells", Exp. Eye Res., 72:581-590(2001).

Jones et al., "Altered Expression of Secreted Frizzled-Related Protein-2 in Retinitis Pigmentosa Retinas", Investigative Ophthalmology and Visual Science, 41:1297-1301 (2000).

Jones et al., "Modulated expression of secreted Frizzled-related proteins in human retinaldegeneration", Neuroreport, 11:3963-3967 (2000).

Kaufman et al., "Ocular effects of oral lithium in humans", ACTA Ophthalmologica, 63:327-332 (1985).

Leclerc et al., "Indirubins Inhibit Glycogen Synthase Kinase-3β and CDK5/P25, Two Protein Kinases Involved in Abnormal Tau Phosphorylation in Alzheimer's Diseases", J. Biol. Chem., 276(1):251-260 (2001) listed as Garnier et al. in appln.

Leost et al., "Paullones are potent inhibitors of glycogen synthase kinase-3β and cyclin-dependent kinase 5/p25", Eur. J. Biochem., 267:5983-5994 (2001).

Lucas JJ, et al., "Decreased nuclear •-catenin, tau hyperphosphorylation and neurodegeneration in GSK-3• conditional transgenic mice", The EMBO Journal 20(1):27-39 (2001).

Meijer et al., "Inhibition of cyclin-dependent kinases, GSK-3β and CK1 by hymenialdisine, a marine sponge constitutent", Chem. & Bio., 7:51-63 (2000) Listed as Thunnissen et al. in application.

Ryves, WJ and Harwood AJ, "Lithium Inhibits Glycogen Synthase Kinase-3 by Competition for Magnesium",Biochemical Biophysics Research Communications, 280:720-725 (2001).

Smith et al., "3-Anilino-4-arylmaleimides: Potent and Selective Inhibitors of Glycogen Synthase Kinase-3 (GSK-3)", Bioorganic & Med. Chem. Letters, 11:635-639 (2001).

Tong et al., "Activation of glycogen synthase kinase 3 beta (GSK-3β) by platelet activating factor mediates migration and cell death in cerebellar granule neurons", European Journal of Neuroscience, 13:1913-1922 (2001).

Craig et al., "Glaulcoma Genetics: Where are we? Where will we go?", Current Opinion in Ophthalmology, 10(2):126-134 (1999).

EP 02799603.2 Supplementary European Search Report dated May 7, 2007.

* cited by examiner

INHIBITORS OF GLYCOGEN SYNTHASE KINASE-3 (GSK-3) FOR TREATING GLAUCOMA

This application claims priority from PCT/US02/30059 filed on Sep. 23, 2002, which claims priority from U.S. Provisional Application No. 60/325,390, filed on Sep. 27, 2001.

The present invention is directed to inhibitors of glycogen synthase kinase-3 for lowering and controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated, but no apparent loss of visual function has occurred; such patients are considered to be a high risk for the eventual development of the visual loss associated with glaucoma. Some patients with glaucomatous field loss have relatively low intraocular pressure. These so called normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

SUMMARY OF THE INVENTION

The present invention is directed to inhibitors of GSK-3 which can be used to treat glaucomatous optic neuropathy and/or lower and control IOP associated with normal-tension glaucoma, ocular hypertension, and/or glaucoma in warm blooded animals, including man. The compounds are formulated in pharmaceutical compositions suitable for topical delivery to the eye.

DESCRIPTION OF THE PREFERRED EMBODIMENTS

Elevated intraocular pressure (IOP) is often an indicator of glaucoma. Left unchecked, continual and long term elevated IOP can contribute to the progressive deterioration of the retina and the loss of visual function. Therefore, lowering IOP is often an objective in the treatment of glaucoma patients in order to decrease the potential for or severity of glaucomatous retinopathy. It has been shown that even those glaucoma patients who do not exhibit elevated levels of IOP benefit from agents that lower and control IOP. Unfortunately, some individuals do not respond well when treated with certain existing glaucoma therapies.

Wnt proteins comprise a large family of structurally related ligands that activate the Wnt signaling pathway. The frizzle family of proteins are key components in this pathway serving as membrane bound receptors for Wnt. The frizzle proteins are a family of seven transmembrane proteins that have an N-terminal extracelluar cysteine rich domain and a cytoplasmic carboxylate tail. Binding of Wnt to frizzle initiates a cascade of events one of which results in the inhibition of (GSK-3) preventing the phosphorylation of β-catenin. Phosphorylation of β-catenin leads to its degradation. Activation of the Wnt pathway increases the intracellular concentration of uncomplexed β-catenin which can activate β-catenin-T cell factor/Lymphoid enhancer factor (TCF/Lef) dependent gene transcription.

Frizzle Related Proteins (FRP) are a family of secreted proteins with cysteine rich regions that are homologous to those of the frizzle family of proteins but lack the membrane-spanning segments of the frizzle proteins. The secreted FRP acts to antagonize the Wnt signaling pathway by binding extracelluar Wnt and preventing it from interacting with frizzle proteins or by forming a nonfunctional complexes with the frizzled receptor. Bafico et al. (1999).

Recently it has been discovered that frizzled related protein (FRP) is differentially expressed in a number of glaucomatous trabecular meshwork cell lines. Perfusion of FRP-1 through perfused human ocular anterior segments maintained in culture resulted in a decrease in flowrate and a corresponding decrease in β-catenin protein levels in the ciliary body and the trabecular meshwork (TM). The decreased flow rate in the cultured anterior segments models an increase in resistance to outflow (increase in intraocular pressure) in intact eye. These results show that there is an active Wnt signaling pathway in the TM and ciliary body and suggest that this pathway is responsible at least in part for maintaining outflow through the TM and thereby controlling IOP.

Since the intracellular level of β-catenin is at least partially regulated by its phosphorylation by GSK-3, inhibition of GSK-3 results in the increase in uncomplexed soluble β-catenin irrespective of the levels of FRP. GSK-3 inhibitors circumvent the FRP mediated antagonism of the Wnt signaling pathway caused by the elevated levels of FRP and counteract the increase in outflow resistance that results from the increase in production of FRP in individuals with glaucoma.

Increased expression of FRP was also detected in the retinas from human donors having retinitis pigmentosa (RP). RP is a family of degenerative diseases that effect the photoreceptors and causes blindness. Since FRP stimulates apoptosis in neurons in vitro the presence of elevated FRP suggests that FRP mediated disruption of Wnt signaling may be involved in retinal degeneration. Although glaucoma is the selective loss of retinal ganglion cells and not photoreceptor cells toxicity mediated by increased expression of FRP or by other mechanism governed by a GSK-3 mediated pathway may contribute to the loss of retinal ganglion cells in glaucoma. Therefore GSK-3 inhibitors would treat the loss of retinal ganglion and also reduce intraocular pressure by increasing aqueous humor outflow.

While not being bound by theory the inventors believe that inhibition of GSK-3 will lower and control normal or elevated intraocular pressure (IOP) and treat glaucomatous optic neuropathy. Compounds that act as GSK-3 inhibitors are well known and have shown a variety of utilities, primarily for disorders or conditions associated with diabetes, dementias such as Alzheimer's disease and manic depression. U.S. Pat. No. 6,057,117 discloses the use of selective inhibitors of GSK-3 for the treatment of diseases that are mediated by GSK-3 activity including diabetes mellitus. WO 00/38675 discloses a method of treatment of conditions associated with a need for the inhibition of GSK-3, such as diabetes, conditions associated with diabetes, chronic neurodegenerative conditions including dementias such as Alzheimer's disease, manic depression, mood disorders such as schizophrenia, neurotraumatic disorders such as acute stroke, hair loss and cancer. WO 00/21927 discloses certain pyrrole-2,5-dione derivatives that are GSK-3 inhibitors for the treatment of diabetes, dementias such as Alzheimer's disease and manic depression. WO 01/56567 describes 2,4-dimainothiazole derivatives and their use as GSK-3 inhibitors, WO 01/49709 describes peptide inhibitors of GSK-3, WO 01/47533 discloses the development of modulatory strategies for the treatment of various diseases. WO 01/41768 discloses the use of hymenialdisine or derivatives for inhibiting cyclin dependent kinases, GSK-3 beta and casein kinase 1 for treating neurodegenerative disorders such as Alzheimer's disease, diabetes, inflammatory pathologies and cancers. WO 01/37819 discloses the use of indirubine derivatives for making medicines inhibiting GSK-3 beta.

Certain paullones analogs have been reported (Leost et al. 2000) to be GSK-3 inhibitors. These compounds were proposed to be useful in the study and possible treatment of neurodegenerative and proliferative disorders.

3-Anilino-4-arylmaleimides have been reported to be potent and selective inhibitors of GSK-3 (Smith et al. 2001).

Hymenialdisine is an inhibitor of GSK-3. It was suggested to have potential in treating neurodegenerative disorders (Thunnissen et al. 2000).

The protein kinase C inhibitors GF1092 and Ro 31-8220 have been reported to be inhibitors of GSK-3 (Tavare et al. 1999).

Indirubines inhibit GSK-3 (Garnier et al. 2001). A potential application for the use of the indirubines as a treatment of neurodegenerative disorders was disclosed.

GSK-3 inhibitors SB-415286 and SB216763 protected both central and peripheral neurons grown in culture from death induced by reduced phosphatidyl inositol pathway activity (Cross et al. 2000).

The use of these compounds to lowering and controlling normal or elevated intraocular pressure (IOP) and to treat glaucoma has not been disclosed.

This invention is directed at the treatment of glaucoma by the inhibition of GSK-3. It is contemplated that any GSK-3 inhibiting compound will be useful in the methods of the present invention. The inventors contemplate that any of the compounds disclosed in WO 00/38675; WO 00/21927; Coglan et al. 2000; Leost et al. 2001; Smith et al. 2001; Garnier et al. 2001; Cross et al. 2001; Thunnissen et al. 2000; Tavare et al. 1999 (as discussed above, all herein incorporated by reference) will be particularly useful.

In one preferred embodiment, the compound for use in the methods of the invention will be selected from compounds defined in WO 00/21927, EP 470490, WO 93/18766, WO 93/18765, EP 397060, WO 98/11103, WO 98/11102, WO 98/04552, WO 98/04551, DE 4243321, DE 4005970, DE 3914764, WO 96/04906, WO 95/07910, DE 4217964, U.S. Pat. No. 5,856,517, U.S. Pat. No. 5,891,901, WO 99/42100, EP 328026, EP 384349, EP 540956, DE 4005969, or EP 508792.

Preferred compounds include compounds of the formula:

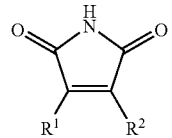

wherein $R^1$ and $R^2$ independently=

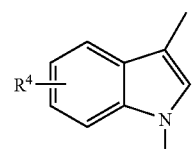

A

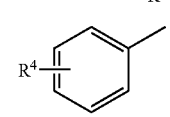

B

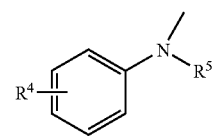

C $R^3$=H, $C_{1-6}$alkyl, (un)substituted phenyl, $C_{1-6}$alkyl-$NR^6R^7$, $C_{1-7}$cycloalkyl, $C_{1-6}$alkyl-$OR^6$, $C_{1-6}$alkylC(O)$_2R^5$, $C_{1-6}$alkylC(O)$NR^6R^7$;

$R^4$=H, or one or more substituents $C_{1-6}$alkyl, (un)substituted phenyl, —$OR^6$, —$SR^6$, halogen, (un)substituted phenoxy, —CN, —NO$_2$, $C_{1-6}$alkyl-$NR^6R^7$, —$NR^6R^7$, $C_{1-7}$cycloalkyl, (un)substituted heterocyclyl, —C(O)$_2R^5$, $C_{1-6}$alkylC(O)$_2R^5$, $C_{1-6}$alkylC(O)$NR^6R^7$; and $R^5$, $R^6$, $R^7$=H, $C_{1-6}$alkyl, (un)substituted phenyl.

Preferably, $R^1$=A, B; $R^2$=B, C;

$R^3$=H, $C_{1-6}$alkyl, $C_{1-6}$alkyl-$NR^6R^7$, $C_{1-6}$alkyl-$OR^6$, $C_{1-6}$alkylC(O)$_2R^5$, $C_{1-6}$alkylC(O)$NR^6R^7$;

$R^4$=H, or one or more substituents $C_{1-6}$alkyl, (un)substituted phenyl, —$OR^6$, halogen, (un)substituted phenoxy, —$NO^2$, $C_{1-6}$alkyl-$NR^6R^7$, —$NR^6R^7$, (un)substituted heterocyclyl, —C(O)$_2R^5$, $C_{1-6}$alkylC(O)$_2R^5$, $C_{1-6}$alkylC(O)$NR^6R^7$; and $R^5$, $R^6$, $R^7$=H, $C_{1-3}$alkyl.

The most preferred compounds for use in the methods of the invention include:

3-(1-[3-aminopropyl]-3-indoyl)-4-(2-chlorophenyl)pyrrole-2,5-dione and 3-(1-[3-hydroxypropyl]-3-indolyl)-4-(2-chlorophenyl)pyrrole-2,5-dione.

In other embodiments, compounds useful in the methods of the invention will be selected from the indirubine analogs defined in WO 01/37819. Generally preferred compounds include indirubine, 5-iodo-indirubine-3'monoxime, 5-(hydroxyethylsulfonamide) indirubine, indirubine-3'-monoxime, 5-(methyl)sulfonamide indirubine, and 5-(dimethyl) sulfonamide indirubine.

Additional embodiments of the invention include the use of compounds selected from the 2,4-diaminothiazole analog defined in WO 01/37819. Preferred compounds include:

(4-amino-2-phenylaminothiazol-5-yl)cyclopropylmethanone,
(4-amino-2-phenylaminothiaol-5-yl)-(4-fluorophenyl)methanone,
(4-amino-2-phenylaminothiazol-5-yl)phenylmethanone,
(4-amino-2-phenylaminothiazol-5-yl)pyridin-3-ylmethanone,
1-(4-amino-2-phenylaminothiazol-5-yl)prpan-1-one
(4-amino-2-phenylaminothiazol-5-yl)-3,4-difluorophenyl)methanone,
(4-amino-2-phenylaminothiazol-5-yl)-3-fluorophenyl)methanone,
(4-amino-2-phenylaminothazol-5-yl)naphthalen-2-ylmethanone,
(4-amino-2-phenylaminothiazol-5-yl)biphenyl-4-ylmethanone,
4-amino-2-phenylaminothiazol-5-yl)-(3-benzyloxyphenyl)methanone,
[4-amino-2-(4-bromophenylamino)thiazol-5-yl]cyclopropylmethanone,
(4-amino-2-phenylaminothiazol-5-yl)-3,4-dichlorophenyl)methanone,
(4-amino-2-phenylaminothiazol-5-yl)-3-methylbenzo[b]thiophen-2-yl)methanone,
(4-amino-2-phenylaminothiazol-5-yl)-(2-methoxyphenyl)methanone,
(4-amino-2-phenylaminothiazol-5-yl)-(3-methoxyphenyl)methanone,
(4-amino-2-phenylaminothiazol-5-yl)-(4-methoxyphenyl)methanone,
(4-amino-2-phenylaminothiazol-5-yl)-(4-chloro-3-methylphenyl)methanone,
(4-amino-2-propylaminothiazol-5-yl)pyridin-3-yl-methanone,
(4-amino-2-phenylaminothiazol-5-yl)pyridin-2-yl-methanone,
(4-amino-2-phenylaminothiazol-5-yl)-pyridinyl-4-yl-methanone,
(4-amino-2-phenylaminothiazol-5-yl)thiophen-2-yl-methanone,
(4-amino-2-phenylaminothiazol-5-yl)thiophen-3-ylmethanone,
(4-amino-2-phenylaminothiazol-5-yl)-(2,6-difluorophenyl)methanone,
(4-amino-2-phenylaminothiazol-5-yl)-(2,6-dichlorophenyl)methanone,
1-(4-amino-2-phenylaminothiazol-5-yl)ethanone,
[4-amino-2(pyridin-3-ylamino)thiazol-5-yl]methanone,
[4-amino-2-(pyrdin-3-ylamino)thiazol-5-yl]phenylmethanone,
[4-amino-2-(3-methoxypropypylamino)thiazol-5-yl]pyridin-3-ylmethanone,
3-[4-amino-5(pyridine-3-carbonyl)thiazol-2-ylamino]butyric acid ethyl ester
[4-amino-2-(3,4-dichlorophenylamino)thiazol-5-yl]-(3-benzyloxyphenyl)methanone,
[4-amino-2-(4-chlorophenylamino)thiazol-5-yl]-(3-benzyloxyphenyl)methanone, and
(4-amino-2-ethylaminothiazol-5-yl)phenylmethanone.

In still another embodiment, compounds selected from the 1,2,4-triazole-carboxylic acid derivative or analog defined in WO 01/09106 will be useful in the methods of the invention. Preferred 1,2,4-triazole-carboxylic acid derivatives include:
3-amino-5-anilino-2-benzoyl-1,2,4-triazole,
3-amino-5-anilino-2-(3,4-methylenedioxybenzoyl)-1,2,4-triazole,
3-amino-5-anilino-2-(3-trans-(2-furylacryloyl)1,2,4-triazole,
3-amino-5-anilino-1-(3-trans-(2-furylacryloyl)1,2,4-triazole,
3-amino-5-anilino-1,2,4-triazole-2-carboxylic acid phenylamide,
3-amino-5-anilino-1,2,4-triazole-2-carboxylic acid cyclohexylamide,
3-amino-5-anilino-1,2,4-triazole-1-carboxylic acid cyclohexylamide,
3-amino-5-(5-chloro-2-methylanilino)-2-benzoyl-1,2,4-triazole,
3-amino-5-anilino-2-(4-chlorobenzoyl)-1,2,4-triazole,
3-amino-5-anilino-2-(2-naphthoyl)1,2,4-triazole,
3-amino-5-anilino-2-(3-bromobenzoyl)-1,2,4-triazole,
3-amino-5-anilino-2-(4-phenylbenzoyl)-1,2,4-triazole,
3-amino-5-anilino-2-(4-trifluoromethylbenzoyl)-1,2,4-triazole,
3-amino-5-anilino-2-((3-benzoyl)benzoyl)-1,2,4-triazole,
3-amino-5-anilino-2-(4-biphenylacetyl)-1,2,4-triazole,
3-amino-5-anilino-2-(2-theinylacetyl)-1,2,4-triazole,
3-amino-5-(3-chloroanilino)-2-phenylthioacetyl-1,2,4-triazole,
3-amino-5-(3-chloroanilino)-2-(2-naphthylacetyl)-1,2,4-triazole,
3-amino-5-anilino-2-(phenoxybenzoyl)-1,2,4-triazole,
3-amino-5-(3-chloroanilino)-2-benzoyl)-1,2,4-triazole,
3-amino-5-anilino-2-cyclohexylcarbonyl-1,2,4-triazole,
3-amino-5-anilino-2-phenylacetyl-1,2,4-triazole,
3-amino-5-anilino-2-(3-nicotinyl)-1,2,4-triazole,
3-amino-5-anilino-2-(3,5-dichlorobenzoyl)-1,2,4-triazole,
3-amino-5-anilino-2-(4-acetylbenzoyl)-1,2,4-triazole,
3-amino-5-anilino-2-(3-indolylacetyl)-1,2,4-triazole,
3-amino-5-anilino-2-(4-fluorophenylacetyl)-1,2,4-triazole,
3-amino-5-anilino-2-(3-bromobenzoyl)-1,2,4-triazole,
3-amino-5-(3-chloroanilino)-2-(3-benzoylpropanoyl)-1,2,4-triazole,
3-amino-5-anilino-2-(cyclopent-2-enyl)acetyl-1,2,4-triazole,
3-amino-5-(3-chloroanilino)-2-(3-benzoylbutyroyl)-1,2,4-triazole,
3-amino-5-(3-chloroanilino)-2-(3,3-diphenylpropanoyl)-1,2,4-triazole,
3-amino-5-anilino-1,2,4-triazole-2-carboxylic acid 4-biphenylamide,
3-amino-5-anilino-1,2,4-triazole-2-carboxylic acid(4-phenoxyphenyl)amide,
3-amino-5-anilino-1,2,4-triazole-2-carboxylic acid(4-bromo-2-methylphenyl)amide,
3-amino-5-anilino-1,2,4-triazole-2-carboxylic acid(1-naphthyl)amide,
3-amino-5-anilino-1,2,4-triazole-2-carboxylic acid(3-methoxyphenyl)amide,
3-amino-5-(4-methoxyanilino)-1,2,4-triazole-2-carboxylic acid(4-chlorophenyl)amide, and
3,5-diamino2-benzoyl-1,2,4-triazole.

Hymenialdisine or derivative or analog defined in WO 01/41768 may also be useful in certain embodiments of the invention. Preferred such compounds include:
Hymenialdisine(4-(2-amino-4-oxo-2-imidazolin-5-ylidene)-4,5,6,7-tetrahydropyrrolo(2,3-c)azepine-8-one),
4-(2-amino-4-oxo-2-imidazolin-5-ylidene)-2-bromo-4,5,6,7-tetrahydropyrrolo(2,3-c)azepine-8-one, and
(4-(2-amino-4-oxo-2-imidazolin-5-ylidene)-3-bromo-4,5,6,7-tetrahydropyrrolo(2,3-c)azepine-8-one.

Other embodiments of the invention include the use of paullone analogs, including 9-nitropaullone, 9-bromopaullone, 9-chloropaullone, and 9-bromo-12-methoxycarbonylmethypaullone in the methods of the invention.

The Compounds of this invention, can be incorporated into various types of ophthalmic formulations for delivery to the eye (e.g., topically, intracamerally, or via an implant). The Compounds are preferably incorporated into topical ophthalmic formulations for delivery to the eye. The Compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the Compound in a hydrophilic base prepared from the combination of, for example, carbopol-974, or the like, according to the published formulations for analogous ophthalmic preparations; preservatives and tonicity agents can be incorporated.

The Compounds are preferably formulated as topical ophthalmic suspensions or solutions, with a pH of about 4 to 8. The establishment of a specific dosage regimen for each individual is left to the discretion of the clinicians. The Compounds will normally be contained in these formulations in an amount 0.01% to 5% by weight, but preferably in an amount of 0.05% to 2% and most preferably in an amount 0.1 to 1.0% by weight. The dosage form may be a solution, suspension microemulsion. Thus, for topical presentation 1 to 2 drops of these formulations would be delivered to the surface of the eye 1 to 4 times per day according to the discretion of a skilled clinician.

The Compounds can also be used in combination with other agents for treating glaucoma, such as, but not limited to, β-blockers, prostaglandins, carbonic anhydrase inhibitors, $\alpha_2$ agonists, miotics, and neuroprotectants.

The following examples are representative of the techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLE 1

GSK-3 Inhibition

Inhibition of GSK-3 can be assayed by the methods described in WO 00/38675. Compounds are evaluated for their ability to inhibit the phosphorylation of a biotinylated peptide derived from the peptide sequence for the phosphorylation site of glycogen synthase. Biot-KYRRAAVPPSPSL SRHSSPHQ(SP)EDEEE is used as the substrate peptide where (SP) is a prephosphorylated serine and S are the three consensus phosphorylation sites for GSK-3 specific phosphorylation. GSK-3 kinase (10 nM final concentration) in a pH 7.0 MOPS buffer containing Tween-20 0.01%, glycerol 5%, 2-mercaptoethanol 7.5 mM, magnesium acetate 10 mM, substrate peptide 8 µM, [γ-$^{33}$P]-ATP 10 µM and inhibitor are incubated at room temperature for 1 hour. The reaction is stopped by the addition of an aqueous mM EDTA solution containing Strepavidin coated SPA beads. Following centrifugation radioactivity is counted using a beta scintillation counter.

EXAMPLE 2

Inhibition of the FRP Induced Reduction in Outflow Rate and β-catenin Levels in Perfused Anterior Segments Human ocular anterior segments are perfused with Dulbecco's modified Eagle's medium (DMEM) at a constant pressure of 11 mm Hg. The outflow rate of each eye is measured by weighing its reservoir at specified periods. After a stabilization period, the eyes are perfused with either vehicle or FRP-1 (10 µg/ml) and their outflow rates monitored for 2-5 days. The perfusion of FRP-1 caused a decrease in aqueous humor outflow. Inhibitor is added and the anterior segment is perfused for an additional 2-4 days. Outflow rate is measured by weighing its reservoir at specific periods.

EXAMPLE 3

| Ingredients | Amount (wt %) |
|---|---|
| Compound of Example 1 | 0.01-2%** |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 4

| Ingredients | Amount (wt %) |
|---|---|
| Compound of Example 1 | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 5

| Ingredients | Amount (wt %) |
|---|---|
| Compound of Example 1 | 0.01-2% |
| Guar gum | 0.4-6.0% |
| Dibasic sodium phosphate (anhydrous) | 0.2% |

-continued

| Ingredients | Amount (wt %) |
| --- | --- |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 6

| Ingredients | Amount (wt %) |
| --- | --- |
| Compound of Example 1 | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. Such substitutions and modifications apparent to those skilled in the art are deemed to be within the spirit, scope and concept of the invention as defined by is the appended claims.

REFERENCES

The following references, to the extent that they provide exemplary procedural or other details supplementary to those set forth herein, are specifically incorporated herein by reference.

Patents
DE 3914764
DE 4005969
DE 4005970
DE 4217964
DE 4243321
EP 328026
EP 384349
EP 397060
EP 470490
EP 508792
EP 540956
U.S. Pat. No. 5,856,517
U.S. Pat. No. 5,891,901
U.S. Pat. No. 6,057,117
WO 93/18765
WO 93/18766
WO 95/07910
WO 96/04906
WO 98/04551
WO 98/04552
WO 98/11102
WO 98/11103
WO 99/42100
WO 00/21927
WO 00/38675
WO 01/09106
WO 01/37819
WO 01/41768
WO 01/47533
WO 01/49709
WO 01/56567

OTHER REFERENCES

Bafico et al., J. BIOL. CHEM., 274(23):16180-16187 (1999)
Leost et al., EUR. J. BIOCHEM., 267:5983-5994 (2001)
Smith et al., BIOORGANIC & MED. CHEM. LETTERS, 11:635-639 (2001)
Thunnissen et al., CHEM. & BIO., 7:51-63 (2000)
Tavare et al., FEBS LETTERS, 460:433-436 (1999)
Cross et al., J. NEUROCHEM., 77:94-102 (2001)
Coglan et al., CHEM. & BIO., 7(10):793-803 (2000)
Gamnier et al., J. BIOL. CHEM., 276(1):251-260 (2001)

We claim:

1. A method for treating glaucomatous optic neuropathy comprising administering to a patient in need thereof a therapeutically effective amount of a composition comprising at least one glycogen synthase kinase-3 (GSK-3) inhibitor in a pharmaceutically acceptable carrier, wherein said GSK-3 inhibitor is a compound of the formula:

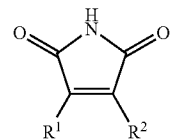

wherein $R^1$ and $R^2$ independently=

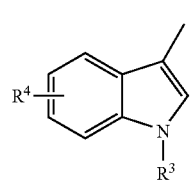
A

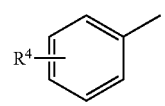
B

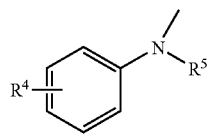
C $R^3$=H, $C_{1-6}$alkyl, (un)substituted phenyl, $C_{1-6}$alkyl-$NR^6R^7$, $C_{1-7}$cycloalkyl, $C_{1-6}$alkyl-$OR^6$, $C_{1-6}$alkylC$(O)_{2R5}$, or $C_{1-6}$alkylC(O)$NR^6R^7$;

$R^4$=H, or one or more substituents $C_{1-6}$alkyl, (un)substituted phenyl, —$OR^6$, —$SR^6$, halogen, (un)substituted phenoxy, —CN, —$NO_2$, $C_{1-6}$alkyl-$NR^6R^7$, —$NR^6R^7$, $C_{1-7}$cycloalkyl, (un)substituted heterocyclyl, —$C(O)_2R^5$, $C_{1-6}$alkyl$C(O)_2R^5$, or $C_{1-6}$alkylC(O)$NR^6R^7$; and $R^5$, $R^6$, $R^7$=H, or $C_{1-6}$alkyl, (un)substituted phenyl.

2. The method of claim 1, wherein $R^1$=A, B; $R^2$=B, C;

$R^3$=H, $C_{1-6}$alkyl, $C_{1-6}$alkyl-$NR^6R^7$, $C_{1-6}$alkyl-$OR^6$, $C_{1-6}$alkylC(O)$_2R^5$, or $C_{1-6}$alkylC(O)$NR^6R^7$;

$R^4$=H, or one or more substituents $C_{1-6}$alkyl, (un)substituted phenyl, —$OR^6$, halogen, (un)substituted phenoxy, —$NO_2$, $C_{1-6}$alkyl-$NR^6R^7$, —$NR^6R^7$, (un)substituted heterocyclyl, —$C(O)_2R^5$, or $C_{1-6}$alkylC(O)$_2R^5$, $C_{1-6}$alkylC(O)$NR^6R^7$; and $R^5$, $R^6$, $R^7$=H, or $C_{1-3}$alkyl.

3. The method of claim 1 wherein said administering is topical application, intracamerally or via an implant.

4. The method of claim 1, wherein the concentration of said GSK-3 inhibitor in said composition is from 0.01% to 2%.

5. The method of claim 2, wherein said GSK-3 inhibitor is 3-(1-[3-aminopropyl]-3-indoyl)-4-(2-chlorophenyl)pyrrole-2,5-dione or 3-(1-[3-hydroxypropyl]-3-indolyl)-4-(2-chlorophenyl)pyrrole-2,5-dione.

6. A method for lowering intraocular pressure (IOP) in a patient in need thereof said method comprising administering to said patient a therapeutically effective amount of a composition comprising at least one glycogen synthase kinase-3 (GSK-3) inhibitor in a pharmaceutically acceptable vehicle, wherein said GSK-3 inhibitor is a compound of the formula:

$C_{1-7}$cycloalkyl, (un)substituted heterocyclyl, —$C(O)_2R^5$, $C_{1-6}$alkylC(O)$_2R^5$, or $C_{1-6}$alkylC(O)$NR^6R^7$; and $R^5$, $R^6$, $R^7$=H, $C_{1-6}$alkyl, or (un)substituted phenyl.

7. The method of claim 6, wherein $R^1$=A, B; $R^2$=B, C;

$R^3$=H, $C_{1-6}$alkyl, $C_{1-6}$alkyl-$NR^6R^7$, $C_{1-6}$alkyl-$OR^6$, $C_{1-6}$alkylC(O)$_2R^5$, $C_{1-6}$alkylC(O)$NR^6R^7$;

$R^4$=H, or one or more substituents $C_{1-6}$alkyl, (un)substituted phenyl, —$OR^6$, halogen, (un)substituted phenoxy, —$NO_2$, $C_{1-6}$alkyl-$NR^6R^7$, —$NR^6R^7$, (un)substituted heterocycyl, —$C(O)_2R^5$, $C_{1-6}$alkylC(O)$_2R^5$, $C_{1-6}$alkylC(O)$NR^6R^7$; and $R^5$, $R^6$, $R^7$=H, or $C_{1-3}$alkyl.

8. The method of claim 6, wherein said administering is topical application, intracamerally or via an implant.

9. The method of claim 6, wherein the concentration of said GSK-3 inhibitor in said composition is from 0.01% to 2%.

10. The method of claim 6, wherein said patient suffers from glaucoma or ocular hypertension.

11. The method of claim 7, wherein said GSK-3 inhibitor is 3-(1-[3-aminoprpyl]-3-indoyl)-4-(2-chlorophenyl) pyrrole-2,5-dione or 3-(1-[3-hydroxypropyl]-3-indolyl)-4-(2-chlorophenyl)pyrrole-2,5-dione.

12. The method of claim 10, wherein said glaucoma is normal-tension glaucoma.

13. A method for preventing or inhibiting glaucomatous optic neuropathy and controlling intraocular pressure (IOP) in a patient in need thereof, said method comprising at least one glycogen synthase kinase-3 (GSK-3) inhibitor in a pharmaceutically acceptable carrier, wherein said GSK-3 inhibitor is a compound of the formula:

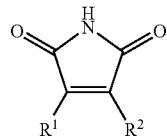

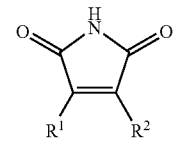

wherein $R^1$ and $R^2$ independently= wherein $R^1$ and $R^2$ independently=

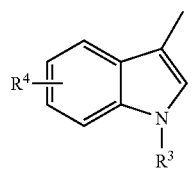

A

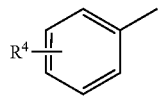

B

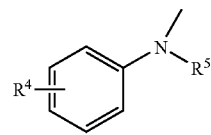

C $R^3$=H, $C_{1-6}$alkyl, (un)substituted phenyl, $C_{1-6}$alkyl-$NR^6R^7$, $C_{1-7}$cycloalkyl, $C_{1-6}$alkyl-$OR^6$, $C_{1-6}$alkylC(O)$_{2R5}$, or $C_{1-6}$alkylC(O)NR6R7;

$R^4$=H, or one or more substituents $C_{1-6}$alkyl, (un)substituted phenyl, —$OR^6$, —$SR^6$, halogen, (un)substituted phenoxy, —CN, —$NO_2$, $C_{1-6}$alkyl-$NR^6R^7$, —$NR^6R^7$, $R^3$=H, $C_{1-6}$alkyl, (un)substituted phenyl, $C_{1-6}$alkyl-$NR^6R^7$, $C_{1-7}$cycloalkyl, $C_{1-6}$alkyl-$OR^6$, $C_{1-6}$alkylC(O)$_{2R5}$, $C_{1-6}$alkylC(O)NR6R7;

$R^4$=H, or one or more substituents $C_{1-6}$alkyl, (un)substituted phenyl, —$OR^6$, —$SR^6$, halogen, (un)substituted phenoxy, —CN, —$NO_2$, $C_{1-6}$alkyl-$NR^6R^7$, —$NR^6R^7$, $C_{1-7}$cycloalkyl,(un)substituted heterocyclyl, $-C(O)_2 R^5$, $C_{1-6}$alkyl$C(O)_2R^5$, or $C_{1-6}$alkyl$C(O)NR^6R^7$; and $R^5$, $R^6$, $R^7$=H, $C_{1-6}$alkyl, or (un)substituted phenyl.

14. The method of claim 13, wherein $R^1$=A, B; $R^2$=B, C;

$R^3$=H, $C_{1-6}$alkyl, $C_{1-6}$alkyl-$NR^6R^7$, $C_{1-6}$alkyl-$OR^6$, $C_{1-6}$alkyl$C(O)_2R^5$, or $C_{1-6}$alkyl$C(O)NR^6R^7$;

$R^4$=H, or one or more substituents $C_{1-6}$alkyl, (un)substituted phenyl, $-OR^6$, halogen, (un)substituted phenoxy, $-NO_2$, $C_{1-6}$alkyl-$NR^6R^7$, $-NR^6R^7$, (un)substituted heterocycyl, $-C(O)_2R^5$, $C_{1-6}$alkyl$C(O)_2R^5$, or $C_{1-6}$alkyl$C(O)NR^6R^7$; and $R^5$, $R^6$, $R^7$=H, or $C_{1-3}$alkyl.

15. The method of claim 13 wherein said administering is topical application, intracamerally or via an implant.

16. The method of claim 13 wherein the concentration of said GSK-3 inhibitor in said composition is from 0.01% to 2%.

17. The method of claim 13, wherein said patient suffers from glaucoma or ocular hypertension.

18. The method of claim 14, wherein said GSK-3 inhibitor is 3-(1-[3-aminopropyl]-3-indoyl)-4-(2-chlorophenyl) pyrrole-2,5-dione or 3-(1-[3-hydroxypropyl]-3-indolyl)-4-(2-chlorophenyl)pyrrole-2,5-dione.

19. The method of 17, wherein said glaucoma is normal-tension glaucoma.

* * * * *

UNITED STATES PATENT AND TRADEMARK OFFICE
CERTIFICATE OF CORRECTION

| | | |
|---|---|---|
| PATENT NO. | : 7,598,288 B2 | Page 1 of 1 |
| APPLICATION NO. | : 10/488496 | |
| DATED | : October 6, 2009 | |
| INVENTOR(S) | : Hellberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1469 days.

Signed and Sealed this

Twenty-eighth Day of September, 2010

David J. Kappos
*Director of the United States Patent and Trademark Office*